United States Patent
Paradkar et al.

(10) Patent No.: US 10,420,718 B2
(45) Date of Patent: Sep. 24, 2019

(54) EFFERVESCENT COMPOSITIONS CONTAINING CO-CRYSTALS OF THE ACID PART

(71) Applicant: University of Bradford, Bradford (GB)

(72) Inventors: Anant Paradkar, Bradford (GB); Sudhir Pagire, Bradford (GB)

(73) Assignee: University of Bradford, West Yorkshire (GB)

(*) Notice: Subject to any disclaimer, the term of this patent is extended or adjusted under 35 U.S.C. 154(b) by 0 days.

(21) Appl. No.: 15/323,266

(22) PCT Filed: Jul. 2, 2015

(86) PCT No.: PCT/GB2015/051942
§ 371 (c)(1),
(2) Date: Dec. 30, 2016

(87) PCT Pub. No.: WO2016/001681
PCT Pub. Date: Jan. 7, 2016

(65) Prior Publication Data
US 2017/0128359 A1    May 11, 2017

(30) Foreign Application Priority Data
Jul. 2, 2014  (GB) ..................................... 1411802

(51) Int. Cl.
| | | |
|---|---|---|
| A61K 31/192 | (2006.01) | |
| A61K 9/00 | (2006.01) | |
| A61K 9/46 | (2006.01) | |
| A61Q 19/10 | (2006.01) | |
| A61K 8/19 | (2006.01) | |
| A61K 8/362 | (2006.01) | |
| A61K 8/49 | (2006.01) | |
| A61K 47/12 | (2006.01) | |
| A61K 47/22 | (2006.01) | |
| A61K 8/34 | (2006.01) | |
| A61K 8/368 | (2006.01) | |

(52) U.S. Cl.
CPC .............. *A61K 9/0007* (2013.01); *A61K 8/19* (2013.01); *A61K 8/347* (2013.01); *A61K 8/362* (2013.01); *A61K 8/368* (2013.01); *A61K 8/4906* (2013.01); *A61K 8/4926* (2013.01); *A61K 8/4953* (2013.01); *A61K 9/0056* (2013.01); *A61K 31/192* (2013.01); *A61K 47/12* (2013.01); *A61K 47/22* (2013.01); *A61Q 19/10* (2013.01); *A61K 2800/222* (2013.01)

(58) Field of Classification Search
None
See application file for complete search history.

(56) References Cited

U.S. PATENT DOCUMENTS

| | | |
|---|---|---|
| 2007/0059356 A1 | 3/2007 | Almarsson et al. |
| 2010/0234577 A1 | 9/2010 | Mazzola et al. |
| 2011/0189277 A1 | 8/2011 | Schultheiss et al. |
| 2011/0236478 A1 | 9/2011 | Dokou et al. |

FOREIGN PATENT DOCUMENTS

| | | |
|---|---|---|
| EP | 2204364 A1 | 7/2010 |
| GB | 514888 A | 11/1939 |
| WO | WO-1999/024592 A1 | 5/1999 |
| WO | WO-2001/080822 A2 | 11/2001 |
| WO | WO-2002/005820 A1 | 1/2002 |
| WO | WO-2002/098388 A2 | 12/2002 |
| WO | WO-2005/117585 A1 | 12/2005 |
| WO | WO-2006/007448 A2 | 1/2006 |
| WO | WO-2006/040764 A2 | 4/2006 |
| WO | WO-2006/040764 A3 | 4/2006 |
| WO | WO-2010/027921 A1 | 3/2010 |
| WO | WO-2011/097372 A2 | 8/2011 |
| WO | WO-2011/150110 A1 | 12/2011 |
| WO | WO-2013/066707 A1 | 5/2013 |
| WO | WO-2013/100871 A1 | 7/2013 |
| WO | WO-2014/007775 A1 | 1/2014 |

OTHER PUBLICATIONS

Arora, et al., "Instability in theophylline and carbamazepine hydrate tablets: cocrystal formation due to release of lattice water," Pharm Res, 30(7): 1779-1789 (2013).
Chen, "Expression and purification of pharmaceutical proteins in plants," Biological Engineering, 1(4): 291-321 (2008).
Elder, et al., "Use of pharmaceutical salts and cocrystals to address the issue of poor solubility," Int J Pharm, 453(1): 88-100 (2012).
Giritch, et al., "Rapid high-yield expression of full-size IgG antibodies in plants coinfected with noncompeting viral vectors," PNAS, 103(40): 14701-14706 (2006).
Hamorsky, et al., "Efficient single tobamoviral vector-based bioproduction of broadly neutralizing anti-HIV-1 monoclonal antibody VRC01 in Nicotiana benthamiana plants and utility of VRC01 in combination microbicides," Antimicrob Agents Ch, 57(5): 2076-2086 (2013).
International Search Report for International Application No. PCT/GB2015/051942 dated Aug. 12, 2015.
Liu, et al., "Recovery and purification process development for monoclonal antibody production," MAbs, 2(5): 480-499 (2010).
Low, et al., "Future of antibody purification," J Chromatogr B, 848(1): 48-63 (2007).
McLean, et al., "Purification of the therapeutic antibody trastuzumab from genetically modified plants using safflower Protein A-oleosin oilbody technology," Transgenic Res, 21(6): 1291-1301 (2012).

(Continued)

*Primary Examiner* — Samantha L Shterengarts
(74) *Attorney, Agent, or Firm* — Foley Hoag LLP; Dana M. Gordon; Alexander J. Chatterley

(57) ABSTRACT

The present invention relates to effervescent compositions which are resistant to water vapor in the atmosphere and to methods of preparing such compositions. In particular, the invention relates to an effervescent composition comprising a co-crystal. The co-crystal comprises an acidic component and a basic component is separate. The co-crystal comprising the acidic component is resistant to water uptake avoiding initiating the effervescence prematurely. Upon dissolution of the co-crystal and the basic component effervescence occurs.

11 Claims, 5 Drawing Sheets

(56) References Cited

OTHER PUBLICATIONS

Pegel, et al., "Evaluating disposable depth filtration platforms for MAb harvest clarification," BioProcess, 9(9): 52-56 (2011).
Shukla, et al., "Downstream processing of monoclonal antibodies—Application of platform approaches," J Chromatogr B, 848(1): 28-39 (2007).
Stein, et al., "The regulation of biologic products derived from bioengineered plants," Curr Opin Biotechnol, 12(3): 308-311 (2001).
Wikipedia, "Baking Powder," available from http://en.wikipedia.org/wiki/Baking_powder [accessed Apr. 27, 2015].
Search Report issued by the Intellectual Property Office in corresponding Application No. GB1411802.0, dated May 1, 2017.

EFFERVESCENT COMPOSITIONS CONTAINING CO-CRYSTALS OF THE ACID PART

RELATED APPLICATIONS

This application is a § 371 national stage application based on Patent Cooperation Treaty Application serial number PCT/GB2015/051942, filed Jul. 2, 2015, which claims the benefit of priority to GB 1411802.0, filed Jul. 2, 2014.

The present invention relates to effervescent compositions which are resistant to water vapour in the atmosphere and to methods of preparing such compositions. In particular, the invention relates to an effervescent composition formed using a co-crystal as one of the components. In the case of the present invention, it is the acidic component which is prepared in the form of a co-crystal.

Effervescent compositions are well known in the prior art and have been used in a variety of applications over a period of time. Numerous patents have also been granted for a variety of different types of formulations. Applications include pharmaceutical compositions, dental and cosmetic compositions, household cleaning agents, beverage sweetening tablets and food supplement tablets, sterilising tablets for water and for sterilising articles for hospital use, and even agrochemicals.

U.S. Pat. No. 4,153,678 discloses levamisole effervescent tablets which are intended to be highly soluble and yield crystal clear solutions in water. The tablets are intended to be stable on storage and easy to use. These tablets are designed for oral administration to animals in predetermined dosages via drinking water. Levamisole is an anti-helminthic preparation for treating swine and presentation in effervescent form presents a number of advantages relative to conventional formulations of that active pharmaceutical ingredient. In these formulations, between 10 and 50% by weight of the active pharmaceutical ingredient (levamisole) in the form of a water soluble salt is formulated with sodium bicarbonate and adipic acid in approximately 1:1 weight ratio and formulated into granules which are then ultimately compressed into tablets. Of course, ultimately, such tablets on exposure to normal atmospheric conditions will absorb water vapour from the air with the consequence that over time such tablets will degrade. There is also the problem that the presence of water vapour in the atmosphere, commonly referred to as conditions of high humidity, will ultimately cause water to be present in sufficient an amount within the formulation to allow reaction between the basic components (sodium bicarbonate) and the acidic component (adipic acid).

U.S. Pat. No. 5,445,827 discloses an effervescent ibuprofen formulation comprising basic granules containing a water soluble ibuprofen salt in combination with, amongst other things, sodium carbonate or potassium carbonate and an acid component. In these formulations the relative ratios between the active pharmaceutical ingredient, ibuprofen, and the acid and basic components are approximately one part by weight of the ibuprofen to 0.1:1 part by weight of the sodium carbonate and 1:4 parts by weight of the acid component. It can therefore be seen that the acid component is presented in significant excess relative to the basic component of the effervescent formulation. In this particular case, the inventors overcame the difficulties caused by the extremely poor solubility of ibuprofen crystals especially when in solution in slightly acidic conditions. This invention employs sodium, potassium and ammonium salts of ibuprofen as the most preferred counter ions though it does also envisage the use of organic counter ions. Irrespective of the manner in which ibuprofen is presented, these formulations also still suffer the problem that once formulated the powders, granules, or tablets of that invention are prone to attack by atmospheric humidity and consequently will suffer degradation over time on exposure to the atmosphere.

WO 02/086048 describes household cleaning compositions which are presented in the form of effervescent tablets. These compositions are presented in compressed form for use in cleaning and/or disinfecting hard surfaces. This invention is intended to avoid the need to provide liquid cleaning and/or disinfecting products which are heavy and bulky. Instead, the consumer is provided with a compressed form of the composition, in the form of tablets, rings, discs, stars, spheres, sticks, pellets, ribbons and briquettes etc. which are then formulated into solution by the consumer at the point of use. These tablets contain an effervescent agent which is an acidic component and a basic component and a germicidal agent. The acidic component may be an organic acid, an organic acid anhydride, an inorganic acid, an inorganic acid salt and mixtures of the aforementioned. The basic component may be a carbonate, bicarbonate, sesquicarbonate and mixtures of these. The same problems accrue to these types of formulations as have been described above in relation to pharmaceutical formulations i.e. the susceptibility to water from the atmosphere. This patent explicitly refers to the fact that the components that comprise the effervescent agents should be very dry because water from the atmosphere can affect the performance of effervescence thereby making the compressed form unusable or causing it to disintegrate very slowly. It also notes that the effervescent agents and the rest of the components should be used, and the final compressed form should be stored, at a temperature of less than room temperature and at a relative humidity of less than 20%. Clearly, exposure to normal atmospheric conditions and water from the atmosphere will be detrimental to these types of effervescent formulations. Indeed, it is often the case that formulations of these type require special packaging in order to protect them from atmospheric conditions.

EP 1953126 describes an effervescent fertiliser which is presented in the form of a single-dose intended to be combined with a specific amount of water. The technical advantage that is said to underlie the invention of this patent resides in the fact that it is supplied in a single-dose of instantly dissolving effervescent fertiliser which is to be used in a specific volume of water equal to a standard volume of a 4 liter watering can. The formulations are presented as tablets which contain a fertiliser component and excipients needed to produce instant dissolution through effervescence. The patent does not, however, provide any details regarding the identity of the excipients.

U.S. Pat. No. 4,725,427 describes effervescent vitamin-mineral granule formulations as food supplements. These compositions are water soluble and contain water soluble and oil soluble vitamins and amino acid chelated minerals in bioavailable form. The compositions are presented as unit dosage formulations weighing between about 2 and 6 g and containing between 20 and 45% citric acid and 5-25% of one or more alkali or alkaline earth metal bicarbonates or carbonate. Once the unit dosage is dissolved in water it provides a flavoured, lightly carbonated drink containing the minerals and vitamins. The compositions are formed in portions consisting of a dry vitamin premix and a separate dry amino acid chelate mineral premix. The two mixes are then blended along with the appropriate flavouring and effervescing materials and packaged in airtight and moisture tight containers. Again, a problem arising with this type of formulation is the susceptibility to water from the atmosphere and it is not only necessary to provide suitable packaging for the final product but appropriate precautions must be taken during preparation of the various premixes to exclude water.

Figure 1:
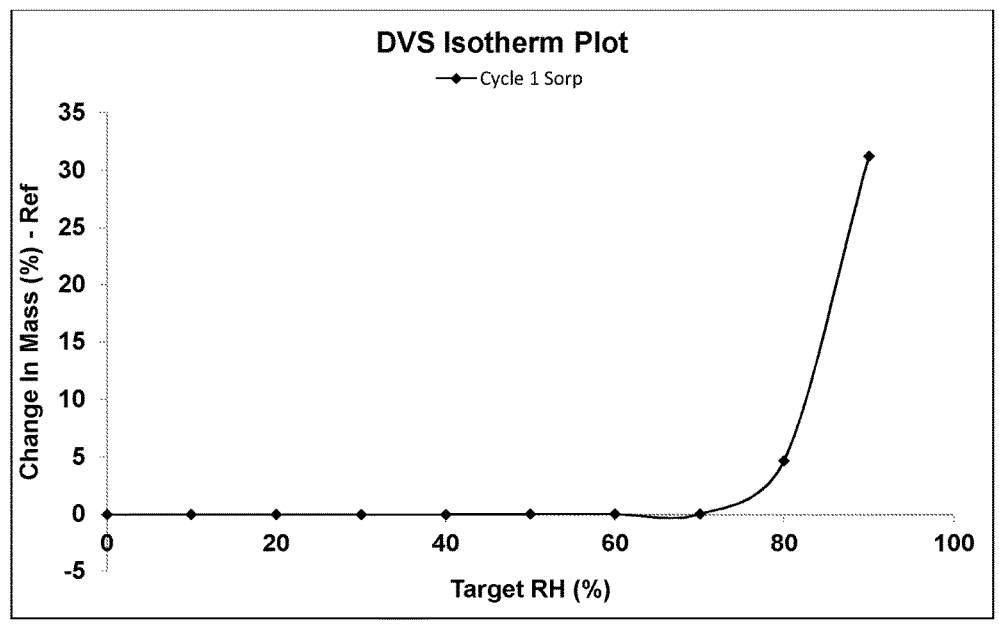
FIG. 1 shows the dynamic vapour sorption (DVS) study plot of the change in mass of citric acid against the relative humidity.

The present invention aims to prepare effervescent formulations which can be conveniently formulated under normal production conditions. It is an aim of the invention to reduce or eliminate the need for special atmospheric conditions when manufacturing and packaging the formulations. It is also an aim of the invention to provide formulations which are stable on standing under normal atmospheric conditions for an extended period of time compared with traditional effervescent formulations. It is also an aim to provide formulations that can be used in more challenging conditions such as at elevated temperatures and/or elevated humidities. Such conditions may be found, for example, in sub-tropical and tropical regions or other humid environments. It is another aim of the invention to provide a formulation in which the acidic component of the co-crystal is present in a very high loading or is 100% of the co-crystal. It is also an aim to provide a formulation which is of low bulk and low weight relative to liquid formulations. The invention aims to avoid problems with bulk storage and transport. It is also an aim to provide a formulation which can be prepared economically and which can be transported and stored economically until re-formulation is required at the point of use by the consumer. It is also an aim to provide a unit-dosage form for convenient re-formulation by the consumer into an appropriate dosage strength. It is also an aim to provide a composition which does not require special packaging and/or storage under special conditions. Issues relating to granulation and tableting include poor compressibility due to low moisture, high compression force required, wear and tear of compression tools, processing at 10 to 20% RH, high dehumidification cost, and shelf life issues associated with the effervescent formulations. These requirements otherwise add to the cost of preparing and keeping the compositions.

The present invention satisfies some or all of the above aims and overcomes the problems in the prior art. The present invention solves some or all of the problems of the prior art formulations by providing an effervescent composition in which one component is presented in the form of a co-crystal.

According to one aspect of the present invention, there is provided an effervescent composition comprising an acidic component and a basic component, wherein the acidic component is in the form of a co-crystal.

According to another aspect of the present invention, there is provided an effervescent composition comprising an acidic component and a basic component, wherein the acidic component is in the form of a co-crystal, and wherein the composition includes one or more agents selected from: an active pharmaceutical ingredient, a sterilising agent, a cleaning agent, a nutritional component, an agrochemical component and an animal health medicament, and optionally one or more excipients.

The definition of the term "co-crystal" has been widely debated in the field of crystallography but is generally accepted as a crystalline structure which is made up of two or more components in a defined stoichiometric ratio. Co-crystals are solids that are crystalline materials composed of two or more molecules in the same crystal. Conventional solid-state forms of an active pharmaceutical ingredient may be classified as being either crystalline, amorphous, or solvate and hydrate forms. Crystalline forms themselves may present in a number of different polymorphic forms each of which usually only contains a single type of molecule within the crystal lattice. Of course, whilst references to crystalline and amorphous forms are being discussed in this application are generally in the context of active pharmaceutical ingredients, since this is one important area of application for the present invention, it is correct to say that polymorphism occurs throughout chemistry and that a wide variety of materials can exhibit polymorphism. Such materials may be presented in non-pharmaceutical applications.

In contrast to single crystal species, co-crystals are distinguishable from traditional pharmaceutical and non-pharmaceutical solid state forms in that co-crystals contain two or more molecules within the same lattice. Thus, for example, in the pharmaceutical field a co-crystal is composed of an active pharmaceutical ingredient together with a neutral guest compound which is frequently referred to as a conformer or a co-former in the crystal lattice. In addition, in contrast to normal single species salts in crystalline form, in which the components in the crystal lattice are in an ionised state, a co-crystal's components are present in a neutral state in the lattice and interact via non-ionic interactions. A co-crystal may be defined as a crystalline material that consists of two or more molecular (and electrically neutral) species held together by non-covalent forces, where both components are solids at room temperature (see S. L. Mohssette, O. Almarsson, M. L. Peterson, J. F. Remenar, M. J. Read, A. V. Lemmo, S. Ellis, M. J. Cima, C R. Gardner, High Throughput crystallisation: polymorphs, salts, co-crystals and solvates of pharmaceutical solids, Adv. Drug DeNv. Rev. 56 (2004) 275-300.)

Hydrates are not considered to be co-crystals. Therefore, co-crystals of the present invention do not encompass hydrates. In other words, the co-former of the present invention may not be water. In addition, the definition of a co-crystal does not include the situation where two materials present in the same vessel crystallise at the same time but in their own separate and individual crystal lattices. This would be considered to be "concurrent crystallisation" rather than the formation of a co-crystal.

The co-crystal formulations of the present invention present a number of advantages. Firstly, they provide the ability to enhance the bioavailability of a pharmaceutical ingredient or the solubility of a non-pharmaceutical ingredient. They also provide the ability to improve the stability of the final formulation and improve its resistance to water vapour from the atmosphere and any water content in the formulation itself in the sense that these formulations are less hygroscopic than conventional formulations. Another technical advantage resides in the ease of processing of the solid material. A further advantage of the formulations of the present invention is that they allow the opportunity to present in crystalline solid state form materials that otherwise lack ionisable functional groups that are required for salt formation and the creation of stable crystal lattices.

The presence of the effervescing agent i.e. both the acidic and basic component in the formulation helps to disintegrate the formulation when mixed with water. In prior art formulations, premature exposure to atmospheric moisture leads to degradation of the known formulations. The formulations of the present invention do not suffer this disadvantage (as will be seen from the data presented below) because of the stability that the acidic component co-crystal imparts to the formulation. Disintegration of the formulations of the present invention occurs in an entirely conventional way and in the same manner as in the prior art once the formulation is added to water. The co-crystal is able to dissolve under these conditions and a chemical reaction can then occur between the acidic and basic component thereby releasing gas. Thus, in an embodiment of the invention the acidic component or an acidic co-former of the co-crystal reacts with the basic component. The acidic and basic components are chosen such that the gas released is carbon dioxide (itself a harmless by-product of the neutralisation process) and it is the gas release which forces the other compressed materials in the formulation to disperse. Once effervescence is complete, the resulting solution can then be used for its intended purpose such as for ingestion to deliver an active pharmaceutical ingredient, application in solution form to plants or crops as a fertiliser or as an insecticide or fungicide, as a sterilising agent for water, as a dental or cosmetic preparation, or as a cleaning agent for surfaces. The resulting solution contains a homogeneous dispersion of the various components of the original composition. Equally, it is not necessary for the formulation to contain an active ingredient for pharmaceutical, agrochemical or cleaning use etc. and the formulation may simply be used to provide a carbonated solution. Such a solution may be used in or added to a beverage such as the Eno™ beverages.

The acidic component which is formed into the co-crystal is typically selected from an organic acid, an organic acid salt, an organic acid anhydride, an inorganic acid, an inorganic acid salt, and mixtures of one or more of the above. The exact identity of the acidic component that is used in the co-crystal will depend on the ultimate purpose of the formulation. Certain classes of acidic component which can be used in principle for gas formation may actually be inappropriate in certain circumstances. For example, in formulations which are intended for pharmaceutical, cosmetic, dental or nutritional use, it is important to ensure that the acidic component is suitable for human or animal consumption and is not toxic or otherwise deleterious to human or animal health. On the other hand, if the formulation is intended as a cleaning agent or as a plant insecticide or fungicide or fertiliser etc. then acidic components that might otherwise be excluded as being harmful by ingestion may also be used.

Ideally, the acidic component is an organic acid such as a carboxylic acid. More preferably the acidic component is a dicarboxylic acid. Carboxylic acids which can be used in the acidic component of the formulations of the present invention include formic acid, propionic acid, malic acid, and tartaric acid. Examples of dicarboxylic acids which can be used in the compositions of the present invention include citric acid, glycolic acid, maleic acid, fumaric acid, adipic acid, succinic acid, lactic acid, gluconic acid, and fumaric acid, and oxalic acid. Sulphamic acid (sometimes known as amidosulphonic acid) can also be used as can similar sulphonic acids. An inorganic acid that may be used is boric acid. Additionally, sulphamic acid and glutaric acid may be the acidic component.

The acidic component can be selected from: formic acid, propionic acid, malic acid, tartaric acid, citric acid, glycolic acid, maleic acid, fumaric acid, adipic acid, succinic acid, lactic acid, gluconic acid, and fumaric acid, oxalic acid, boric acid, sulphamic acid, glutaric acid and sulphamic acid. Optionally, the acidic component can be selected from: citric acid, glycolic acid, maleic acid, fumaric acid, adipic acid, succinic acid, lactic acid, gluconic acid, and fumaric acid, oxalic acid, glutaric acid and sulphamic acid.

The acidic component may be selected from: citric acid, glutaric acid, malic acid, maleic acid, tartaric acid, and fumaric acid.

The basic component of the formulations of the present invention can be selected from carbonates, bicarbonates and sesquicarbonates which are effectively double salts of bicarbonates and carbonates. For example, sodium sesquicarbonate is a double salt of sodium bicarbonate and sodium carbonate. The basic component may be a mixture of one or more of carbonates, bicarbonates and sesquicarbonates. These components will be present in the form of their ammonium, alkali metal or alkaline earth salts. Sodium, potassium, calcium, magnesium and ammonium salts are preferred salts; and sodium, potassium and ammonium salts are especially preferred given their excellent solubility. Of these, sodium and potassium are most preferred (certainly for pharmaceutical, nutritional, cosmetic and dental formulations at least) on account of their solubility and compatibility with physiological media since this feature of utmost importance in formulations intended for pharmaceutical and nutritional uses.

The co-former component (i.e. the guest component of the co-crystal) which is mixed with the acidic component (i.e. the material which ultimately reacts with the basic component) to form the co-crystal may be selected from: ascorbic acid, gallic acid, nicotinamide, isonicotinamide, citric acid, aglutamic acid, histidine, urea, saccharine, glycine, tyrosine, vanillin and valine. The co-former could also be an active ingredient such as an active pharmaceutical ingredient e.g. piroxicam, carbamazepine, and paracetamol. The co-former is a solid at room temperature. The co-former may not be a solvent, for example the co-former may not be water.

The co-former could also be theophylline. The co-former component (i.e. the guest component of the co-crystal) which is mixed with the acidic component (i.e. the material which ultimately reacts with the basic component) to form the co-crystal may be selected from: ascorbic acid, gallic acid, nicotinamide, isonicotinamide, citric acid, malic acid, tartaric acid, aglutamic acid, histidine, urea, saccharine, glycine, tyrosine, vanillin, valine, theophylline, piroxicam, carbamazepine, and paracetamol. The co-former could also be an active ingredient such as an active pharmaceutical ingredient e.g. theophylline, piroxicam, carbamazepine, and paracetamol.

Preferably, the co-former is selected from: nicotinamide, isonicotinamide, urea, peroxicam, theophylline, malic acid and tartaric acid.

The co-crystal formation is based on the structure of the co-formers and co-formers are the most important component of the co-crystal in terms of ensuring a stable lattice structure. Co-crystals can be divided into co-crystal anhydrates, co-crystal hydrates (solvates), anydrates of co-crystals of salts, and hydrates (solvates of co-crystals of salts). The exact identity of the co-crystal will depend on the nature of the acidic component on the one hand and the co-former on the other hand. For example, in the case in which the acidic component is an organic acid such as a carboxylic acid, the co-former may be a material such as nicotinamide, isonicotinamide, glycine, and vanillin. The co-former could also be another acid. In such a case, the acidic component of the co-crystal represents 100% by weight of the co-crystal.

The solvent can sometimes play an important part in the co-crystal formation. The solvent is selected depending on the solubility of the co-former. Solvents that can be used in co-crystal formation include aliphatic alcohols such as methanol, ethanol, isopropanol; acetonitrile; and water.

The formulations of the present invention may include one or more excipients as appropriate to the type of formulation being prepared. Excipients may be selected from one or more of: bulking agents, sweeteners, flavouring agents, lubricants, stabilisers, disintegrating agents, suspending agents, thickening agents, and surfactants.

The effervescent composition may be presented in the form of powder, granules, tablet, or capsule.

The co-crystal contains the acidic component. In certain embodiments the acidic component may comprise two or more different substances as the reactive component. The acidic component may be selected from formic acid, propionic acid, malic acid, tartaric acid, citric acid, glycolic acid, maleic acid, fumaric acid, adipic acid, succinic acid, lactic acid, gluconic acid, and fumaric acid, oxalic acid, glutaric acid, boric acid, and sulphamic acid and similar sulphonic acids. Most preferably, the acidic component is a single substance such as a carboxylic acid. Preferably it is a dicarboxylic acid. The carboxylic acid may be preferably selected from citric acid, tartaric acid, malic acid, maleic acid, glutaric acid, fumaric acid and oxalic acid.

The acidic component represents at least 30% by weight of the co-crystal and more usually is at least 80% and more preferably at least 90% by weight of the co-crystal. In more preferred embodiments, the acidic component represents at least 95% by weight, more preferably at least 98%, and most preferably at least about 100% by weight of the co-crystal.

The co-crystal may be formed from the acidic component and an acidic co-former. Therefore, the co-crystal may be about 100% by weight of acidic molecules. Acidic molecules may refer to the acidic component and an acidic co-former.

The co-crystal and the basic component which are mixed to form the effervescent mix component of the formulations of the present invention are mixed in a ratio of from 1:0.5 mole ratio of co-crystal (based on the acidic component) to 1:10 mole ratio. Usually, it is preferred that the basic component is present in an excess in the effervescent component. Accordingly, in some embodiments it may be preferable that the mole ratio of the co-crystal to the basic component is from 1:5 to 1:10 and more preferably is in the range of from 1:7.5 to 1:10. In other embodiments, it may be preferable that the mole ratio of the co-crystal to the basic component is from 1:2.5 to 1:5 and more preferably is in the range of from 1:3 to 1:4. Thus a typical effervescent formulation containing citric acid and sodium bicarbonate in the weight ratio of 1:1.5 will show a mole ratio of about 1:3.4.

In an embodiment the effervescent composition is substantially free of acids except any acid of the co-crystal (i.e. the acidic component with or without an acidic co-former). In other words, the effervescent composition does not comprise any acid outside the co-crystal. In an embodiment, the effervescent composition comprises one acid, the acidic component of the co-crystal.

The optimum mole ratio will, however, vary depending on the nature of the acidic composition. The preferred mole ratios will depend on whether monobasic, dibasic or tribasic (or higher) acids are being considered and the amount of acidic material in the acidic component. For example, in the case of monocarboxylic acids or other monobasic acids, the relative amount of the acidic component may be higher than that needed for a dibasic acid to compensate for the monobasic nature of the acid.

In an embodiment the co-crystal is not a co-crystal of VX-950 and 4-hydroxybenzoic acid. Furthermore, in the same or an alternative embodiment the co-crystal is not a pterostilbene:glutaric acid co-crystal, pterostilbene:caffeine co-crystal, pterostilbene: carbamazepine co-crystal or apterostilbene:piperazine co-crystal. Preferably, the co-crystal is not a VX-950:4-hydroxybenzoic acid co-crystal or a pterostilbene:glutaric acid cocrystal. Optionally, the co-crystal of the invention does not comprise pterostilbene. Optionally, the co-crystal of the invention does not comprise VX-950.

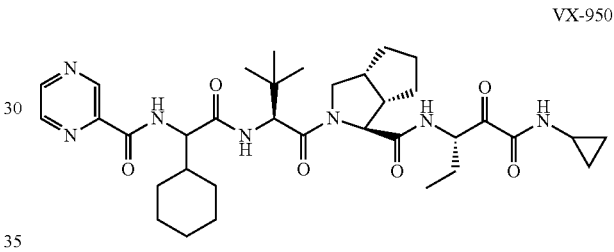

VX-950

Co-crystals can be prepared by a number of methods which can be broadly characterised as solution methods, grinding methods, anti-solvent methods, slurry conversion methods, supercritical fluid methods, and hot melt extrusion methods. All of these are applicable to the present invention. However, in the case of the present invention, the grinding method and hot melt extrusion method are preferred and more particularly the method of choice is a liquid assisted grinding method.

Co-crystals can be characterised by a wider variety of analytical methods. The co-crystals of the present invention can be analysed by powder X-ray diffraction, FT-IR and Raman spectroscopy in order to verify their structure and composition. Other physical methods of characterisation of the co-crystals of the present invention include thermo gravimetric analysis (TGA) and differential scanning calorimetry (DSC).

Typical challenges that occur during manufacturing of conventional formulations relate to the control of humidity since the humidity levels in the effervescent product manufacturing and packaging area need to be very carefully controlled. Granulation must normally occur at less than 20% relative humidity and tableting must generally occur at a temperature of no more than 20-25° C. and less than 30% relative humidity. The packaging process itself must take place at less than 30% relative humidity. In addition, the low moisture content of the effervescent granules themselves provides a challenge during the tableting procedure. Typical pharmaceutical granules for compression will contain 2-4% moisture whereas effervescent granules contain 0.5-1.0% moisture. The compression pressure required for tableting of an effervescent preparation is therefore very high compared to a conventional tablet formulation where the moisture content is higher. This higher pressure that is required for tableting an effervescent formulation leads to wear and tear of the dies and punches in the tableting process and it is frequently necessary to use special alloys to produce the dies and punches for such processes. The formulations of the present invention reduce or overcome these problems and do not necessarily require such high tableting pressures and therefore lead to both economies and convenience in the tableting process. In addition, the use of special alloys for the tableting equipment is less critical.

Another issue that arises with conventional effervescent formulations is that water impermeable packaging is required for packaging known effervescent preparations. In the case of the compositions of the present invention this requirement becomes much less critical. It can therefore be seen from the above that the controlled thermo-hygrometric conditions, high maintenance cost of processing equipment and special packaging materials all conspire to make the manufacture of effervescent preparations expensive and challenging. This in part has led to a more limited application for effervescent preparations than would otherwise be the case. The present invention thus widens the potential field of applications for which effervescent preparations can be used as well as providing substantial technical benefits in those areas where they are used.

The present invention also covers the following numbered clauses:
1. An effervescent composition comprising an acidic component and a basic component, wherein the acidic component is in the form of a co-crystal.
2. An effervescent composition comprising an acidic component and a basic component, wherein the acidic component is in the form of a co-crystal, and wherein the composition includes one or more agents selected from: an active pharmaceutical ingredient, a sterilising agent, a cleaning agent, a nutritional component, an agrochemical component and an animal health medicament, and optionally one or more excipients.
3. A composition as claimed in clauses 1 or 2, wherein the acidic component which is formed into the co-crystal is selected from an organic acid, an organic acid salt, an organic acid anhydride, an inorganic acid, an inorganic acid salt, and mixtures of one or more of the above.
4. A composition according to any preceding clause, wherein the acidic component is a carboxylic acid.
5. A composition according to clause 4, wherein the carboxylic acid is selected from: formic acid, propionic acid, malic acid, tartaric acid, citric acid, glycolic acid, maleic acid, fumaric acid, adipic acid, succinic acid, lactic acid, gluconic acid, and fumaric acid, and oxalic acid, sulphamic acid and similar sulphonic acids.
6. A composition according to any preceding clause, wherein the basic component is selected from: carbonates, bicarbonates and sesquicarbonates.
7. A composition according to clause 6, wherein the basic component is one or more of carbonates, bicarbonates and sesquicarbonates in the form of their ammonium, alkali metal or alkaline earth salts.
8. A composition according to any preceding clause, wherein the co-former component is selected from: ascorbic acid, gallic acid, nicotinamide, isonicotinamide, citric acid, aglutamic acid, histidine, urea, saccharine, glycine, tyrosine, vanillin and valine.
9. A composition according to any preceding clause, wherein the co-crystal and the basic component are present in a ratio of from 1:0.5 mole ratio of co-crystal (based on the acidic component) to 1:10 mole ratio.
10. A composition according to any preceding clause, wherein the acidic agent represents at least 30% by weight of the co-crystal.
11. A composition according to clause 10, wherein the acidic component is about 100% by weight of the co-crystal.

Formulations according to the present invention can be prepared in a two-step process. In the first step the co-crystal of the acidic component is prepared and in the second step the effervescent mixture is prepared by combining this with the basic component.

Thus, in one exemplary embodiment, citric acid was used as the acidic component and it was mixed with nicotinamide as the co-former in a molar ratio of one part citric acid to two parts nicotinamide. The mixture was subjected to grinding for five minutes in the presence of a small amount of methanol. The resulting ground product was confirmed as a citric acid-nicotinamide co-crystal using powder X-ray diffraction (PXRD).

In the second stage of the procedure, the acidic component is combined with the basic component to form an effervescent mixture (i.e. a mixture that efferevesces when dissolved in water). In fact, two separate effervescent mixtures (for the purposes of comparison) were prepared with one being a co-crystal and the other a conventional formulation. A first control effervescent mixture was prepared as a standard formulation, and not in the form of a co-crystal, for the purposes of evaluating its properties relative to an otherwise identical co-crystal formulation according to the invention. The control effervescent mixture contained 1 g of citric acid and 1.5 g of sodium bicarbonate. A second, separate, effervescent mixture was prepared in accordance with the present invention. This mixture was a co-crystal of citric acid and nicotinamide containing the equivalent of 1 g of citric acid together with 1.5 g of sodium bicarbonate. Accordingly, the formulation according to the invention and the control formulation were identical in the nature and quantities of the effervescent components.

The mixtures were exposed to 75% and 98% relative humidity conditions in desiccators for a period of 24 hours. The effervescent action was then evaluated by adding the control and test samples to 1000 ml of water. The control sample was moist and did not show any effervescence even having only been exposed to 75% relative humidity. The control samples exposed to 98% relative humidity did not show any effervescence. In contrast, the test sample was free flowing and showed excellent effervescent action even after storage at 98% relative humidity for 24 hours. In each case, the control sample could not be considered to be free flowing and had absorbed a significant amount of moisture. The samples according to the invention maintained their integrity and their effervescent properties.

The co-crystals were stored at 98% relative humidity and the stability was evaluated after 24 hours using powder X-ray diffraction. There was no change in the powder X-ray diffraction pattern after storage of the formulations according to the invention indicating that there was no dissociation of the co-crystal. This stability of the co-crystal in the presence of high amounts of atmospheric moisture is responsible for maintenance of the effervescent action.

This represents a substantial advantage for the formulations of the present invention. The present invention can thus be seen to avoid unwanted reaction between the acid and basic components of an effervescent formulation in the presence of atmospheric moisture. This provides significant advantages in terms of manufacturing, packaging, storage and ultimate use of the formulations especially in more challenging environments. This advantage leads to a significant reduction in the cost of production without influencing the effervescent action and indeed ensures that the effervescent action is able to persist even after storage periods that would otherwise be impossible for conventional formulations.

The formulations of the present invention thus solve a number of technical problems. Even a small amount of moisture (more than 1%) in the final product will cause a loss of ability of the formulation to cause effervescence when formulated in accordance with known procedures. Accordingly, extreme care has to be taken to avoid moisture during the manufacture, packaging and storage of conventional effervescent formulations. The present invention overcomes all of these difficulties.

The co-crystal of the acidic component can be prepared by neat grinding, liquid assisted grinding, solution crystallisation, hot melt extrusion, solvent evaporation, spray drying, microwave treatment, slurry crystallisation, and high shear mixing. Of these liquid assisted grinding is preferred when formulating compositions for pharmaceutical, cosmetic, dental and nutritional use.

Further co-crystal samples and formulations were prepared by liquid assisted grinding for the purposes of evaluation of the formulations of the present invention. The aim was to prepare co-crystals of some dicarboxylic acids that can be used in effervescent compositions and to demonstrate the stability of such co-crystals at 98% relative humidity. These experiments also compared the stability and effervescent performance in comparison with standard effervescent compositions (i.e. a plain citric acid and sodium bicarbonate system).

The following formulations were prepared:
1. citric acid-nicotinamide 1:2 co-crystal
2. glutaric acid-nicotinamide 1:1 co-crystal
3. glutaric acid-isonicotinamide 1:1 co-crystal
4. L malic acid-L tartaric acid 1:1 co-crystal.
5. Fumaric acid-nicotinamide 1:1 co-crystal
6. Citric acid-urea 1:1 co-crystal
7. Piroxicam-glutaric acid 1:1 co-crystal Additional co-crystals were prepared using a high shear granulator.
8. Citric acid-nicotinamide 1:2 co-crystal
9. Citric Acid-theophylline 1:1 co-crystal These co-crystal formulations were prepared with the following compositions:

EXAMPLE 1. CITRIC ACID-NICOTINAMIDE 1:2 CO-CRYSTAL

Citric acid (1.921 g) and nicotinamide (2.4425 g) were taken in a mortar and subjected to liquid assisted grinding with methanol for 5 min. The resultant product was characterised by X-ray diffractometry (XRD) to confirm the co-crystal formation.

EXAMPLE 2. GLUTARIC ACID-NICOTINAMIDE 1:1 CO-CRYSTAL

Glutaric acid (1.3212 g) and nicotinamide (1.2212 g) were taken in a mortar and subjected to liquid assisted grinding with methanol for 5 min. The resultant product was characterised by X-ray diffractometry (XRD) to confirm the co-crystal formation.

EXAMPLE 3. GLUTARIC ACID-ISONICOTINAMIDE 1:1 CO-CRYSTAL

Glutaric acid (1.3212 g) and isonicotinamide (1.2212 g) were taken in a mortar and subjected to liquid assisted grinding with methanol for 5 min. The resultant product was characterised by X-ray diffractometry (XRD) to confirm the co-crystal formation.

EXAMPLE 4. LMALIC ACID-L TARTARIC ACID 1:1 CO-CRYSTAL

LMalic acid (0.6704 g) and Ltartaric acid (0.7504 g) were taken in a mortar and subjected to liquid assisted grinding with methanol for 5 min. The resultant product was characterised by X-ray diffractometry (XRD) to confirm the co-crystal formation. This is an example of a co-crystal in which the acidic component represents 100% by weight of the crystal.

EXAMPLE 5. FUMARIC ACID-NICOTINAMIDE 1:1 CO-CRYSTAL

Fumaric acid (1.160 g) and nicotinamide (1.221 g) were taken in a mortar and subjected to liquid assisted grinding with methanol for 5 min. The resultant product was characterised by X-ray diffractometry (XRD) to confirm the co-crystal formation.

EXAMPLE 6. CITRIC ACID-UREA 1:1 CO-CRYSTAL

Citric acid (1.921 g) and urea (0.600 g) were taken in a mortar and subjected to liquid assisted grinding with ethanol for 5 min. The resultant product was characterised by X-ray diffractometry (XRD) to confirm the co-crystal formation.

EXAMPLE 7. PIROXICAM-GLUTARIC ACID 1:1 CO-CRYSTAL

Piroxicam (0.828 g) and glutaric acid (0.330 g) were taken in a mortar and subjected to liquid assisted grinding with ethanol for 5 min. The resultant product was characterised by X-ray diffractometry (XRD) to confirm the co-crystal formation.

The stability of the co-crystals to moisture was investigated by storing the co-crystals at 98% relative humidity and the following results were observed. The co-crystal samples were analysed with XRD to check whether the co-crystal retained its structure or became dissociated or degraded over time on exposure to the atmosphere.

EXAMPLE 8. CITRIC ACID-NICOTINAMIDE 1:2 CO-CRYSTAL PREPARED USING A HIGH SHEAR GRANULATOR

Citric acid (55.035 g), nicotinamide (70 g) and hydroxypropyl methyl cellulose (6.25 g) were mixed in a tumbler mixer for 5 minutes. This material was then transferred to the 1 L bowl of the high shear granulator (model-GMX-LAB Micro; Make-Freund Vector). The material was initially blended for 5 minutes at low mixer speed (100 rpm). After 5 minutes, mixer speed was changed to 250 rpm and chopper speed was kept at 1000 rpm, at this stage water was added (6 ml) and mixing was continued for further 25 minutes. After 25 minutes, 4 ml of water was added and mixer and chopper speed were increased to 1000 rpm and 3000 rpm respectively, and were maintained for next 15 minutes. After 15 minutes process was stopped, material was unloaded and characterised for the co-crystal formation using PXRD.

EXAMPLE 9. CITRIC ACID-THEOPHYLLINE 1:1 CO-CRYSTAL PREPARED USING A HIGH SHEAR GRANULATOR

Citric acid (64.507 g), theophylline (60.500 g) and hydroxypropyl methyl cellulose (6.25 g) were mixed in a tumbler mixer for 5 minutes. This material was then transferred to the 1 L bowl of the high shear granulator (model-GMX-LAB Micro; Make-Freund Vector). The material was initially blended for 5 minutes at low mixer speed (100 rpm). After 5 minutes, mixer speed was changed to 250 rpm and chopper speed was kept at 1000 rpm, at this stage water was added (6 ml) and mixing was continued for further 25 minutes. After 25 minutes, 4 ml of water was added and mixer and chopper speed were increased to 1000 rpm and 3000 rpm respectively, and were maintained for next 15 minutes. After 15 minutes process was stopped, material was unloaded and characterised for the co-crystal formation using PXRD.

EXAMPLE 10. PREPARATION OF CO-CRYSTAL USING HOT MELT EXTRUDER

Extruder was pre-heated to the selected processing temperature. A range of barrel temperature profiles were used, typically increasing from a cooled feed zone to a maximum mid way along the barrel and decreasing towards the die end. The maximum temperature of 110° C. was set in the mid way of the barrel and screw configuration 8 was used for this experiment. Extruder screw rotation speed was set to 10 revolutions per minute (rpm). A pre-mixed blend of L-Malic acid (67.0437 g and L-tartaric acid (75.043 g) was then introduced into the feed hopper of the extruder. The extruded mixture was then collected at the exit of the screws. The collected material was subsequently analysed for co-crystal formation using PXRD.

TABLE 1

| Length (diameters) | Element type |
|---|---|
| 6 | Forwarding |
| 2 | 90° |
| 1 | 60° |
| 6 | Forwarding |
| 1.25 | 60° |
| 4 | Forwarding |
| 1 | 90° |
| 1 | 60° |
| 1.25 | 30° |
| 4 | Forwarding |
| 1 | 60° |

TABLE 1-continued

| Length (diameters) | Element type |
|---|---|
| 1 | 30° |
| 9 | Forwarding |
| 1.50 | Discharge |
| 40 | Total length |

EXAMPLE 11. PREPARATION OF THE EFFERVESCENT COMPOSITION

Effervescent compositions were prepared by homogenous mixing of acid (0.8 g) with the sodium bicarbonate (1.2 g) and subjected to stability testing at 75% and 98% relative humidity. In the case of co-crystals, the co-crystal amount equivalent to 0.8 g of the acid was taken. The stability study investigated the change in the physical appearance and effervescent action of the compositions. Saturated sodium chloride and potassium sulphate solution in water was used to maintain the 75% and 98% relative humidity in the desiccator chamber.

Procedure for Effervescence Test

Effervescent composition (2 g) was added rapidly in one portion to 1 L water under stirring at 100 rpm. The time of cessation of effervescence and the time take to obtain a clear solution was noted. The following results were obtained:

Stability of Co-Crystals at 98% RH

TABLE 2

| | XRD results | | | | | | |
|---|---|---|---|---|---|---|---|
| | Day 1 | Day 2 | Day 3 | Day 5 | Day 10 | Day 14 | Day 18 |
| Citric acid-nicotinamide, 1:2 | Co-crystal is stable. No peaks for starting materials | Co-crystal is stable. No peaks for starting materials | Co-crystal is stable. No peaks for starting materials | Co-crystal is stable. No peaks for starting materials | Co-crystal is stable. No peaks for starting materials | Stable | Stable |

TABLE 3

| | XRD results | | | |
|---|---|---|---|---|
| | Day 1 | Day 2 | Day 6 | Day 10 |
| Glutaric acid-nicotinamide, 1:1 | Co-crystal is stable. No peaks for starting materials | Co-crystal is stable. No peaks for starting materials | Stable | Stable |

TABLE 4

| | XRD results | | | |
|---|---|---|---|---|
| | Day 1 | Day 2 | Day 6 | Day 10 |
| Glutaric acid:iso-nicotinamide, 1:1 | Co-crystal is stable. No peaks for starting materials | Co-crystal is stable. No peaks for starting materials | Stable | Stable |

TABLE 5

| | XRD results | | |
|---|---|---|---|
| | Day 1 | Day 2 | Day 3 |
| L malic-L tartaric acid, 1:1 | Co-crystal is stable. No peaks for starting materials | Co-crystal is stable. No peaks for starting materials | Unstable, almost half sample converted to liquid |

EXAMPLE 12. CITRIC ACID EFFERVESCENT COMPOSITION

Citric acid (0.8 g)+sodium bicarbonate (1.2 g) and citric acid-nicotinamide 1:2 co-crystal (1.8170 g) equivalent to citric acid (0.8 g)+sodium bicarbonate (1.2 g) subjected to stability testing and tested for physical appearance and effervescence.

TABLE 6

| | Citric acid/sodium bicarbonate system | | | |
|---|---|---|---|---|
| | 75% RH | | 98% RH | |
| Day | Physical appearance | Effervescence | Physical appearance | Effervescence |
| Day 0 | No lumps or no moist mass | Effervescence cessation: 14 sec Clear solution: 1 min | No lumps or no moist mass | Effervescence cessation: 14 sec Clear solution: 1 min |
| Day 1 | Hard mass | No effervescence | Hard moist mass | No effervesce |
| Day 2 | Hard mass | No effervescence | Hard mass | No effervescence |
| Day 3 | Hard mass | No effervescence | Hard mass | No effervescence |

TABLE 7

| | Citric acid- nicotinamide co-crystal/sodium bicarbonate system | | | |
|---|---|---|---|---|
| | 75% RH | | 98% RH | |
| Day | Physical appearance | Effervescence | Physical appearance | Effervescence |
| Day 0 | No lumps or no moist mass | Effervescence cessation: 40 sec Clear solution: 2 min | No lumps or no moist mass | Effervescence cessation: 40 sec Clear solution: 2 min |
| Day 1 | No lumps, No moist mass, dry mass | Effervescence cessation: 12 sec Clear solution: 1 min 45 sec | No lumps, No moist mass, dry mass | Effervescence cessation: 14 sec Clear solution: 1 min 55 sec |
| Day 2 | No lumps, almost dry and free powder mass | Effervescence cessation: 10-12 sec Low intensity Clear solution: 1 min 50 sec | No lumps, almost dry and free powder mass | Effervescence cessation: 10-15 sec Low intensity Clear solution: 2 min 10 sec |

TABLE 7-continued

| | Citric acid- nicotinamide co-crystal/sodium bicarbonate system | | | |
|---|---|---|---|---|
| | 75% RH | | 98% RH | |
| Day | Physical appearance | Effervescence | Physical appearance | Effervescence |
| Day 3 | Almost free flowing mass, no lumps or moist | Effervescence cessation: 10-12 sec Low intensity Clear solution: 1 min 40 sec | Almost free flowing mass, no lumps or moist | Effervescence cessation: 14-18 sec Low intensity Clear solution: 1 min 30 sec |

EXAMPLE 13. GLUTARIC ACID EFFERVESCENT COMPOSITION (NICOTINAMIDE SYSTEM)

Glutaric acid (0.8 g)+sodium bicarbonate (1.2 g) and glutaric acid-nicotinamide 1:1 co-crystal (1.54 g) equivalent to glutaric acid (0.8 g)+sodium bicarbonate (1.2 g) were subjected to stability testing and tested for physical appearance and effervescence.

TABLE 8

| | Glutaric acid/sodium bicarbonate system | | | |
|---|---|---|---|---|
| | 75% RH | | 98% RH | |
| Day | Physical appearance | Effervescence | Physical appearance | Effervescence |
| Day 0 | No lumps or no moist mass | Effervescence cessation: 14 sec Clear solution: 1 min 40 sec | No lumps or no moist mass | Effervescence cessation: 14 sec Clear solution: 1 min 40 sec |
| Day 1 | Moist mass | Effervescence cessation: 11 sec Clear solution: 1 min 43 sec | Deliquescence started, some liquid mass + solid mass | Effervescence cessation: 6 sec Clear solution: 1 min 14 sec |
| Day 2 | Moist mass | No effervescence Clear solution: 1 min | Complete liquid | No effervescence |
| Day 3 | Paste like mass | No effervescence Clear solution: 1 min | Discontinued | |

TABLE 9

| | Glutaric - nicotinamide co-crystal/sodium bicarbonate system | | | |
|---|---|---|---|---|
| | 75% RH | | 98% RH | |
| Day | Physical appearance | Effervescence | Physical appearance | Effervescence |
| Day 0 | No lumps or no moist mass | Effervescence cessation: 23 sec Clear solution: 1 min 40 sec | No lumps or no moist mass | Effervescence cessation: 23 sec Clear solution: 1 min 40 sec |

TABLE 9-continued

Glutaric - nicotinamide co-crystal/sodium bicarbonate system

| | 75% RH | | 98% RH | |
|---|---|---|---|---|
| Day | Physical appearance | Effervescence | Physical appearance | Effervescence |
| Day 1 | No lumps or no moist mass | Effervescence cessation: 39 sec Clear solution: 2 min 10 sec | Slightly moisten but no lumps | Effervescence cessation: 21 sec Clear solution: 1 min 49 sec |
| Day 2 | No lumps or slightly moisten | Effervescence cessation: 15 sec Clear solution: 4 min 40 sec | Highly moist mass, lumps, paste like mass at the bottom | Effervescence cessation: Almost no effervescence Clear solution: 4 min 10 sec |
| Day 3 | No lumps, Moist powder mass | Effervescence cessation: 10 sec Clear solution: 5 min 15 sec | | |

Glutaric Acid Composition (Isonicotinamide System)

Glutaric acid (0.8 g)+sodium bicarbonate (1.2 g) and glutaric acid-nicotinamide 1:1 co-crystal (1.54 g) equivalent to glutaric acid (0.8 g)+sodium bicarbonate (1.2 g) were subjected to stability testing and tested for physical appearance and effervescence.

TABLE 10

Glutaric acid/sodium bicarbonate system

| | 75% RH | | 98% RH | |
|---|---|---|---|---|
| Day | Physical appearance | Effervescence | Physical appearance | Effervescence |
| Day 0 | No lumps or no moist mass | Effervescence cessation: 14 sec Clear solution: 1 min 40 sec | No lumps or no moist mass | Effervescence cessation: 14 sec Clear solution: 1 min 40 sec |
| Day 1 | Moist mass | Effervescence cessation: 11 sec Clear solution: 1 min 43 sec | Deliquescence started, some liquid mass + solid mass | Effervescence cessation: 6 sec Clear solution: 1 min 14 sec |
| Day 2 | Moist mass | No effervescence Clear solution: 1 min | Complete liquid | No effervescence |
| Day 3 | Paste like mass | No effervescence Clear solution: 1 min | Discontinued | |

TABLE 11

Glutaric - isonicotinamide co-crystal/sodium bicarbonate system

| | 75% RH | | 98% RH | |
|---|---|---|---|---|
| Day | Physical appearance | Effervescence | Physical appearance | Effervescence |
| Day 0 | No lumps or no moist mass, free flowing powder | Effervescence cessation: 21 sec Clear solution: 2 min 15 sec | No lumps or no moist mass, free flowing powder | Effervescence cessation: 21 sec Clear solution: 2 min 15 sec |
| Day 1 | No lumps or no moist mass, free flowing powder | Effervescence cessation: 22 sec Clear solution: 3 min | Very slightly moist and few lumps | Effervescence cessation: 15 sec Clear solution: 3 min 15 sec |
| Day 2 | Slightly moist but no lumps | Effervescence cessation: 14-16 sec Clear solution: 4 min 10 sec | Complete moist and big lumps | No Effervescence |
| Day 3 | Slightly moist but no lumps | Effervescence cessation: 14 sec Clear solution: 1 min 27 sec | Complete moist and big lumps | No Effervescence |

EXAMPLE 14. LMALIC AND L TARTARIC ACID COMPOSITION

LMalic and L tartaric acid in 1:1 molar ratio (0.8 g)+sodium bicarbonate (1.2 g) and L malic and L tartaric acid co-crystals in 1:1 molar ratio (0.8 g)+sodium bicarbonate were subjected to stability testing and tested for physical appearance and effervescence.

TABLE 12

L malic and L tartaric acid/sodium bicarbonate system

| | 75% RH | | 98% RH | |
|---|---|---|---|---|
| Day | Physical appearance | Effervescence | Physical appearance | Effervescence |
| Day 0 | No lumps or no moist mass | Effervescence cessation: 16 sec Clear solution: 50 sec | No lumps or no moist mass | Effervescence cessation: 16 sec Clear solution: 50 sec |
| Day 1 | Moist mass, paste like | No effervescence | Moist mass, paste like | No effervesce |
| Day 2 | Discontinued | | Discontinued | |

TABLE 13

L malic acid -L tartaric acid co-crystal/sodium bicarbonate system

| | 75% RH | | 98% RH | |
|---|---|---|---|---|
| Day | Physical appearance | Effervescence | Physical appearance | Effervescence |
| Day 0 | No lumps or no moist mass | Effervescence cessation: 18 sec Clear solution: 50 sec | No lumps or no moist mass | Effervescence cessation: 18 sec Clear solution: 50 sec |
| Day 1 | Slightly moist mass | Effervescence cessation: 20 sec Clear solution: 1 min 06 sec | Moist mass, paste like | No effervescence |
| Day 2 | moist mass and big lumps | very slight effervescence, low intensity and for 10 sec Clear solution: 50 sec | complete moist mass, like thick paste | No Effervescence |
| Day 3 | Big lump, complete moist mass | very slight effervescence, low intensity and for 12 sec Clear solution: 1 min 14 sec | Moist to deliquescent mass | No Effervescence |

EXAMPLE 15

Effervescent tablets containing citric acid/nicotinamide 1:2 co-crystal as a source of acid were compared in terms of effervesce performance with a tablet containing citric acid when stored at 75% and 98% relative humidity. The tablet had the ingredients shown in the table below.

TABLE 14

| Name of Ingredients | Co-crystal containing effervescent tablet (mg/tablet) | Standard effervescent tablet (mg/tablet) |
|---|---|---|
| Citric acid/nicotinamide co-crystal | 204 | — |
| Citric acid | — | 90 |
| Sodium bicarbonate | 135 | 135 |
| Mannitol | 125 | 125 |
| Microcrystalline cellulose, Avicel PH302 | 100 | 100 |
| Lactose, pharmatose | 40 | 40 |
| Magnesium stearate | 10 | 10 |

All ingredients listed in above table were sieved through #355μ. The amounts of each ingredient required for one tablet were weighed accurately and mixed for 2 minutes to get the homogenous mixture. This mixture was then compressed under 1 Ton pressure with a dwell time of 30 sec. The tablets were stored at 40%, 75% and 98% relative humidity and tested for their physical appearance and effervescence performance.

TABLE 15

Tablet with Plain citric acid

| | 75% RH | | 98% RH | |
|---|---|---|---|---|
| Day | Physical appearance | Effervescence | Physical appearance | Effervescence |
| Day 0 | Smooth white surface, | Effervescence cessation: 39 sec | | |
| Day 1 | Rough, off-white surface | Effervescence cessation: 12 sec | All tablets are broken | No effervescence |
| Day 2 | Surface is slightly swollen and rough | Effervescence cessation: 4 sec. Almost no effervescence | Discontinued | |
| Day 3 | Surface is slightly swollen and rough | Effervescence cessation: No effervescence | Discontinued | |

TABLE 16

Tablet with Citric acid/nicotinamide co-crystal

| | 75% RH | | 98% RH | |
|---|---|---|---|---|
| Day | Physical appearance | Effervescence | Physical appearance | Effervescence |
| Day 0 | Smooth white surface | Effervescence cessation: 57 sec | | |
| Day 1 | Smooth white surface | Effervescence cessation: 45 sec | All tablets are broken | No effervescence |
| Day 2 | Smooth surface, No moisture | Effervescence cessation: 45 sec | Discontinued | |
| Day 3 | Smooth surface | Effervescence cessation: 1 min 40 sec. Slow effervescence and disintegration of tablet | Discontinued | |

TABLE 17

Tablet with Plain citric acid

| | 40% RH | |
|---|---|---|
| Day | Physical appearance | Effervescence |
| Day 0 | Smooth white surface | Effervescence cessation: 39 sec |
| Day 1 | Rough, off-white surface | Effervescence cessation: 24 sec |
| Day 2 | Surface is slightly swollen and rough | Effervescence cessation: 30 sec. Low intensity of effervescent action |
| Day 3 | Rough, off-white surface | Effervescence cessation: 8 sec. Intensity is very low |

TABLE 18

Tablet with Citric acid/nicotinamide co-crystal

40% RH

| Day | Physical appearance | Effervescence |
|---|---|---|
| Day 0 | Smooth white surface | Effervescence cessation: 39 sec |
| Day 1 | Smooth white surface | Effervescence cessation: 1 min 28 sec Slow effervescence |
| Day 2 | Smooth surface | Effervescence cessation: 2 min Slow effervescence but good intensity |
| Day 3 | Smooth white surface | Effervescence cessation: 1 min 15 sec Good intensity of effervescence |

As a comparison with a marketed effervescent formulation, we investigated the physical stability at 98% relative humidity of the effervescent formulation, ENO (effervescent powder formulation), which is marketed by GlaxoSmithKline (GSK) as a gastrointestinal product. This product is an antacid powder which is mixed with water to produce a sparkling antacid drink for the temporary relief of heartburn & indigestion caused by too much food and drink. Each 5 g of powder contains: sodium bicarbonate PhEur 2.32 g, citric acid PhEur 2.18 g, anhydrous sodium carbonate PhEur 0.50 g, and each 5 g of powder contains 0.85 g of sodium. The stability is indicated in Table 19 below.

TABLE 19

| At 0 min | Free flowing powder, No moisture |
|---|---|
| After 2 hrs | Hard cake, moist |
| After 24 hrs | Complete liquid |

EXAMPLE 16. IBUPROFEN EFFERVESCENT GRANULES

Ibuprofen effervescent formulations were prepared as described below to check their stability at elevated relative humidity conditions. The ibuprofen effervescent formulations are granules and tablets formulations. We aimed to study the stability of effervescent formulation containing plain acid in the effervescent composition against the effervescent composition containing acid in the co-crystal form. The composition of ibuprofen effervescent granules is mentioned in the below table

TABLE 20

| | Quantity (g) | |
|---|---|---|
| Name of ingredient | Standard effervescent granules | Co-crystal containing effervescent granules |
| Ibuprofen sodium salt | 3.3195 | 3.3195 |
| Sodium bicarbonate | 34.0925 | 34.0925 |
| Polyvinylyrrolidone (PVP K30) | 3 | 3 |
| Citric acid | 9.875 | — |
| Citric acid-nicotinamide 1:2 co-crystal | — | 22.48 |

Ibuprofen, sodium bicarbonate and PVP K30 were sieved through #355μ sieve and weighed accurately. These materials were then blended to produce an homogenous mass and granulated with water as a granulation liquid. The wet granules were dried at 60° C. for 2 hrs and then sieved through #355μ sieve. This portion was designated as the API portion. On the other hand, citric acid and co-crystal including citric acid was sieved through #355μ sieve separately; these were designated acid portion A and acid portion B, respectively. Then the API portion was admixed with the acid portion A and B separately in the appropriate proportions to obtain the effervescent compositions.

EXAMPLE 17. IBUPROFEN EFFERVESCENT TABLETS

TABLE 21

| Name of Ingredients | Standard effervescent tablet (g/tablet) | Co-crystal containing effervescent tablet (g/tablet) |
|---|---|---|
| Ibuprofen sodium salt | 0.2213 | 0.2213 |
| Sodium bicarbonate | 0.6818 | 0.6818 |
| Polyvinylyrrolidone (PVP K30) | 0.1 | 0.1 |
| Mannitol | 0.150 | 0.150 |
| Citric acid | 0.198 | — |
| Citric acid-nicotinamide 1:2 co-crystal | — | 0.4486 |

All ingredients listed in above table were sieved through #355μ. The amount of each ingredient required for one tablet was weighed accurately and mixed for 2 minutes to get the homogenous mixture. This mixture was then compressed under 0.5 Ton pressure with Dwell time of 10 sec.

A comparative stability study of ibuprofen effervescent granules and tablets was then conducted. The granules and tablets were stored at 45%, 75% and 98% relative humidity and tested for their physical appearance and effervescence performance. The results are shown below.

TABLE 22

Granules of Ibuprofen salt with Plain citric acid

| | 75% RH | | 98% RH | |
|---|---|---|---|---|
| Day | Physical appearance | Effervescent performance | Physical appearance | Effervescent performance |
| After 6 Hrs | Water droplets, some bubbles | Not done | Hard mass, complete moist | Not done |
| Day 1 | Hard and porous mass, big lumps | Almost no effervescence | Hard and porous mass, big lumps | Almost no effervescence |
| Day 2 | | Discontinued | | Discontinued |
| Day 3 | | Discontinued | | Discontinued |

TABLE 23

Granules of Ibuprofen salt with Citric acid/nicotinamide co-crystal

| Day | 75% RH Physical appearance | 75% RH Effervescent performance | 98% RH Physical appearance | 98% RH Effervescent performance |
|---|---|---|---|---|
| After 6 Hrs | Slightly moisten | Not done | Slightly moisten | Not done |
| Day 1 | Slightly moist, no lumps and almost free flowing | Good effervescence For 50 sec. Clear solution: 1:50 min | Slightly moist, no lumps and almost free flowing | Good effervescence For 1 min. Clear solution: 1:33 min |
| Day 2 | Compare to day 1 sample is more moist, no lumps | Good effervescence For 40 sec. Clear solution: 1:40 min | Compare to day 1 sample is more moist, no lumps | Good effervescence For 47 sec. Clear solution: 1:42 min |
| Day 3 | Moist mass and few lumps | Good effervescence For 1.15 min. Clear solution: 1:45 min | Considerably moist mass and lumps | Less effervescence For 20 sec. Clear solution: 1:30 min |

TABLE 24

Granules of Ibuprofen salt with Plain citric acid

45% RH

| Day | Physical appearance | Effervescent performance |
|---|---|---|
| Day 1 | Moist mass, some small lumps | Good effervescence For 30 sec. Clear solution: 1:10 min |
| Day 2 | Moist mass, some small lumps | Good effervescence For 40 sec. Clear solution: 1:10 min |
| Day 3 | Moist mass and lumps | Good effervescence For 30 sec. Clear solution: 1:20 min |

TABLE 25

Granules of Ibuprofen salt with Citric acid/nicotinamide co-crystal

45% RH

| Day | Physical appearance | Effervescent performance |
|---|---|---|
| Day 1 | Very slightly moist mass, no lumps, free flowing | Good effervescence For 1 min. Clear solution: 1:50 min |
| Day 2 | Slightly moist mass | Good effervescence For 57 sec. Clear solution: 1:50 min |
| Day 3 | Slightly moist mass | Good effervescence For 54 sec. Clear solution: 1:50 min |

TABLE 26

Tablets of Ibuprofen salt with Plain citric acid

| Day | 75% RH Physical appearance | 75% RH Effervescent performance | 98% RH Physical appearance | 98% RH Effervescent performance |
|---|---|---|---|---|
| 0 Day | Smooth and dried surface | Good effervescence For 4 min. Clear solution: 5 min | Same as 75% RH | Same as 75% RH |
| After 4 Hrs | Some reaction might have took place, bubbles observed on the surface | Not done | Some reaction might have took place, bubbles observed on the surface | Not done |
| Day 1 | Surface is rough, bubbles on the surface, tablet was adhered to the weighing boat | Very slow and low intensity of effervescence Clear solution: 9.10 min | Surface is rough, bubbles on the surface, shape slightly damaged, tablet was adhered to the weighing boat | Almost no effervescence For 2.37 min. Clear solution: 8.30 min |
| Day 2 | Surface is rough, bubbles on the surface, tablet was adhered to the weighing boat | Almost no effervescence | Surface is rough and porous, tablet is deformed | Almost no effervescence |

TABLE 26-continued

Tablets of Ibuprofen salt with Plain citric acid

| | 75% RH | | 98% RH | |
|---|---|---|---|---|
| Day | Physical appearance | Effervescent performance | Physical appearance | Effervescent performance |
| Day 3 | Surface is very rough and bubbles on the surface, tablet was adhered to weighing boat | Almost no effervescent | Tablet is deformed and completely wetted, there is generation of liquid near tablet | No effervescence |

TABLE 27

Tablets of Ibuprofen salt with Citric acid/nicotinamide co-crystal

| | 75% RH | | 98% RH | |
|---|---|---|---|---|
| Day | Physical appearance | Effervescent performance | Physical appearance | Effervescent performance |
| 0 Day | Smooth and dried surface | Good effervescence For 3.10 min. Clear solution: 4.25 min | Same as 75% RH | Same as 75% RH |
| After 4 Hrs | No change up to 1 hr | Not done | No change up to 1 hr | Not done |
| Day 1 | Smooth surface, no change in the tablet appearance | Good effervescence For 3 min. Clear solution: 6 min | Smooth surface but slightly moist, no change in the tablet appearance | Good effervescence For 2.37 min. Clear solution: 5 min |
| Day 2 | Smooth surface, no change in the tablet appearance | Good effervescence For 4.00 min. Clear solution: 4.30 min | Moist surface, few cracks on the surface | Slow effervescence For 50 sec. Tablet disintegrates completely Clear solution: 2.25 min |
| Day 3 | Smooth surface, no change in the tablet appearance | Good effervescence For 2.10 min. Clear solution: 3 min | Tablet is deformed and completely wetted, there is generation of liquid near tablet | No effervescence |

TABLE 28

Tablets of Ibuprofen salt with Plain citric acid

45% RH

| Day | Physical appearance | Effervescent performance |
|---|---|---|
| 0 Day | Same as 75% RH | Same as 75% RH |
| Day 1 | Rough surface, bubbles on the tablet surface, tablet was adhered to the weighing boat | Good effervescence For 2.50 min. Clear solution: 3.52 min |
| Day 2 | Rough surface, bubbles on the surface, moist, tablet was adhered to the weighing boat | Slow effervescence For 3.15 min. Clear solution: 5.10 min |
| Day 3 | Rough surface and moist mass | Very slow effervescence For 5 min. Clear solution: 6.10 min |

TABLE 29

Tablets of Ibuprofen salt with Citric acid/nicotinamide co-crystal

45% RH

| Day | Physical appearance | Effervescent performance |
|---|---|---|
| 0 Day | Same as 75% RH | Same as 75% RH |
| Day 1 | Smooth surface, no change in the tablet appearance | Good effervescence For 3.40 min. Clear solution: 5:10 min |
| Day 2 | Smooth surface, no change in the tablet appearance | Good effervescence For 3.50 min. Clear solution: 4.25 min |

TABLE 29-continued

Tablets of Ibuprofen salt with Citric acid/nicotinamide co-crystal 45% RH

| Day | Physical appearance | Effervescent performance |
|---|---|---|
| Day 3 | Smooth surface, no change in the tablet appearance | Good effervescence For 3.10 min. Clear solution: 4.15 min |

EXAMPLE 18. EFFERVESCENT BATH SALT CONTAINING CITRIC ACID-NICOTINAMIDE 1:2 CO-CRYSTAL AND IT'S STABILITY IN COMPARISON WITH BATH SALT CONTAINING A STANDARD COMPOSITION AT 45%, 75% AND 98% RH FOR 3 DAYS

Effervescent bath salt was prepared containing acid in standard form and acid in the form of co-crystal and the comparative stabilities were measured under different humidity conditions. Bath salts are water-soluble, usually inorganic, solid products designed to be added to water during bathing. They are said to improve cleaning, improve the experience of bathing, and serve as a vehicle for cosmetic agents. Bath salts have been developed which mimic the properties of natural mineral baths or hot springs. Chemically speaking, all bath salts are true salts but the more organic salts commonly used in bath water (especially surfactants like soap) are not called "bath salts" because those appear more like wax or oil instead. Such salts include magnesium sulfate (Epsom salts), sodium chloride (table salt), sodium bicarbonate (baking soda), sodium hexametaphosphate (Calgon, amorphous/glassy sodium metaphosphate), sodium sesquicarbonate, borax, and sodium citrate. Fragrances and colours are often added to bath salts; in fact, one purpose of salts is as a vehicle or diluents to extend fragrances which are otherwise too potent for convenient use. Other common additives to bath salts are oils (agglomerating the salts to form amorphous granules, the product being called bath beads or bath oil beads), foaming agents, and effervescent agents.

The effervescent bath salts contain an acid (citric acid) and an alkali (baking soda). When they are sitting in a jar, they are both in a dry powder form so they don't react. However, as soon as they are placed in bathwater they dissolve and the components can react. That chemical reaction creates the effervescence.

Compositions were prepared as follows.

TABLE 30

| Name of ingredient | Quantity (g) | |
|---|---|---|
| | Standard effervescent bath salt | Co-crystal containing effervescent bath salt |
| Bath salt, sodium chloride | 1.14 | 1.14 |
| Sodium bicarbonate | 0.57 | 0.57 |
| Citric acid | 0.285 | — |
| Citric acid-nicotinamide 1:2 co-crystal | — | 0.647 |

First, bath salt in the form of sodium chloride, and sodium carbonate were mixed to produce an homogenous mixture. To this mixture is added the acid portion to produce the final effervescent composition.

The bath salt formulations were stored at 45%, 75% and 98% relative humidity to check its stability and the results are shown below.

TABLE 31

Bath salt with Plain citric acid

| | 75% RH | | 98% RH | |
|---|---|---|---|---|
| Day | Physical appearance | Effervescent performance | Physical appearance | Effervescent performance |
| After 1 hrs | No change | Not performed | Slightly moist mass | Not performed |
| After 6 hrs | Moist mass | Not performed | Hard, fused, moist mass | Not performed |
| After 11 hrs | Hard, fused, moist mass | Not performed | Hard, fused, moist mass | |
| Day 1 | Hard, fused, moist mass | Few effervescence as hard mass disintegrates Clear solution: 1 min 53 sec | Hard, fused, moist mass | No effervescence |
| Day 2 | Hard, fused, moist mass | No effervescence | Almost all liquid | No effervescence |
| Day 3 | Hard, fused, moist mass | No effervescence | Liquid | No effervescence |

TABLE 32

Bath salt with Citric acid/nicotinamide co-crystal

| | 75% RH | | 98% RH | |
|---|---|---|---|---|
| Day | Physical appearance | Effervescent performance | Physical appearance | Effervescent performance |
| After 1 hrs | No change | Not performed | No change | Not performed |
| After 6 hrs | No change | Not performed | No change | Not performed |
| After 11 hrs | No change | Not performed | No change | Not performed |
| Day 1 | Free mass, not moist | Good intense effervescence for 25 sec Clear solution: 1 min 30 sec | Few loose lumps, slightly wetted | Slow and low intense effervescence for 45 sec Clear solution: 2 min 30 sec |
| Day 2 | Loose lumps but not moist | Good intense effervescence for 25 sec Clear solution: 1 min 45 sec | Some solid undergo liquid state | NO effervescence |
| Day 3 | Loose lumps but not moist | Good intense effervescence for 27 sec Clear solution: 1 min 50 sec | Almost all liquid | NO effervescence |

TABLE 33

Bath salt with Plain citric acid

45% RH

| Day | Physical appearance | Effervescent performance |
|---|---|---|
| After 11 hrs | No change | Not performed |
| Day 1 | Slightly hard mass, fused | Good effervescence For 15 sec Clear solution: 1 min 45 sec |
| Day 2 | Hard, fused mass | Low intensity effervescence for 16 sec. Clear solution after 1 min 15 sec |
| Day 3 | Hard, fused mass | Low intensity effervescence for 20 sec. Clear solution after 1 min 40 sec |

TABLE 34

Bath salt with Citric acid/nicotinamide co-crystal

45% RH

| Day | Physical appearance | Effervescent performance |
|---|---|---|
| After 11 hrs | No change | Not performed |
| Day 1 | Free flowing mass, no moisture | Good intense effervescence For 20 sec Clear solution: 1 min 30 sec |
| Day 2 | Free flowing mass, not moist | Good intense effervescence For 38 sec Clear solution: 1 min 50 sec |
| Day 3 | Free flowing mass, not moist | Good intense effervescence For 30 sec Clear solution: 1 min 55 sec |

EXAMPLE 19. EFFECT OF CO-CRYSTAL PURITY ON THE STABILITY OF EFFERVESCENT COMPOSITION

The effect of purity of the co-crystal on the stability of effervescent composition during storage was investigated. This study investigated the importance of purity of acid co-crystals prepared by different methods and its effect on to stability of the effervescent composition. The reason for looking at this is that there are chances of getting impurities in the form of unreacted acid during co-crystal synthesis which might be attributed to slight changes in the processing parameters or during scale-up. Thus, it is important to check the effect of acid co-crystal impurities on to stabilisation of effervescent composition and determine whether there is tolerance to a small degree of impurity.

Citric acid-nicotinamide, 1:2, co-crystals were prepared by the solvent assisted grinding method and formation of co-crystal was confirmed using PXRD.

For the experimental purpose 5%, 10%, 15%, 20% and 30% of citric acid (by weight) was added as an impurity to above prepared co-crystals. This co-crystal with known acid impurities was used to prepare the effervescent compositions. These compositions were then subjected to stability study at 75% and 98% RH. The stability samples were checked for their physical appearance and effervescent action for three days.

Effervescence test was performed using 500 ml of water at 100 rpm and time for which effervescence action remains and gives clear solution was noted.

The results are shown below.

TABLE 35

Citric acid/nicotinamide co-crystal with 5% citric acid impurity

| | 75% RH | | 98% RH | |
|---|---|---|---|---|
| Day | Physical appearance | Effervescent performance | Physical appearance | Effervescent performance |
| Day 1 | | Small loose lumps, disturbed upon shaking Effervescence: Good, 27 sec Clear: 1 min 15 sec | | Small loose lumps Effervescence: Good, 25 sec Clear: 1 min 10 sec |
| Day 2 | | Loose, moist cake (dump mass) stuck to bottom Effervescence: OK, 24 sec Clear: 58 sec | | Loose, moist cake (dump mass) stuck to bottom Effervescence: OK, 30 sec Clear: 1 min 08 sec |
| Day 3 | | Loose cake, moist mass, stuck to bottom Effervescence: OK, 23 sec, clear: 1 min 40 sec | | Loose cake, moist mass, stuck to bottom Effervescence: Slow and low intensity, 43 sec, clear: 1 min 33 sec |

TABLE 36

Citric acid/nicotinamide co-crystal with 10% citric acid impurity

| | 75% RH | | 98% RH | |
|---|---|---|---|---|
| Day | Physical appearance | Effervescent performance | Physical appearance | Effervescent performance |
| Day 1 | | loose lumps which stuck to bottom Effervescence: slow, 30 sec Clear: 1 min 36 sec | | loose lumps which stuck to bottom Effervescence: slow, 25 sec Clear: 1 min 26 sec |
| Day 2 | | Loose cake, moist, stuck to bottom Effervescence: OK, 35 sec Clear: | | Loose cake, moist, stuck to bottom Effervescence: Slow, low intensity, 30 sec |

TABLE 36-continued

Citric acid/nicotinamide co-crystal with 10% citric acid impurity

| | 75% RH | | 98% RH | |
|---|---|---|---|---|
| Day | Physical appearance | Effervescent performance | Physical appearance | Effervescent performance |
| | | 1 min 15 sec | | Clear: 1 min 20 sec |
| Day 3 | | Hard granular mass, stuck to bottom Effervescence: OK, 26 sec, clear: 56 sec | | Hard cake, fused mass, stuck to bottom Effervescence: slow low intensity start after 7-8 sec for 56 sec, clear: 1 min 45 sec |

TABLE 37

Citric acid/nicotinamide co-crystal with 15% citric acid impurity

| | 75% RH | | 98% RH | |
|---|---|---|---|---|
| Day | Physical appearance | Effervescent performance | Physical appearance | Effervescent performance |
| Day 1 | | Loose, compact, moist mass. Stuck to bottom Effervescence: slow, 15-20 sec, clear: 1 min 18 sec | | Loose, compact, moist mass. Stuck to bottom Effervescence: slow, 15 sec, clear: 52 sec |
| Day 2 | | Loose, compact, moist mass. Stuck to bottom Effervescence: slow, 25 sec, clear: 1 min 04 sec | | Loose, compact, moist mass. Stuck to bottom Effervescence: slow, 30 sec, clear: 1 min 10 sec |
| Day 3 | | Hard cake, stuck to bottom Effervescence: Slow, low intensity, 20 sec, clear: 1 min 13 sec | | Hard cake, fused mass, paste like, stuck to bottom Effervescence: Slow, low intensity Start after 17 sec for 40 sec, clear: 1 min 25 sec |

TABLE 38

| | 75% RH | | 98% RH | |
|---|---|---|---|---|
| Day | Physical appearance | Effervescent performance | Physical appearance | Effervescent performance |
| Citric acid/nicotinamide co-crystal with 20% citric acid impurity | | | | |
| Day 1 | | Loose, compact, moist mass. Stuck to bottom Effervescence: slow, 45 sec, clear: 1 min 04 sec | | Loose, compact, moist mass. Stuck to bottom Effervescence: slow, low intense 40 sec, clear: 1 min 15 sec |
| Day 2 | | Moist, hard cake, stuck to bottom, Effervescence: Slow, 28 sec, clear: 1 min 10 sec | | Moist, hard cake, stuck to bottom, Effervescence: Slow and low intensity, 15 sec, clear: 1 min 20 sec |
| Day 3 | | Loose cake, hard granular mass, stuck to bottom Effervescence: Slow, 30 sec, clear: 58 sec | | Hard cake, fused mass, paste like, stuck to bottom Effervescence: Slow, low intensity Start after 15 sec for 45 sec, clear: 1 min 35 sec |
| Citric acid/nicotinamide co-crystal with 30% citric acid impurity | | | | |
| Day 1 | | Loose cake, moist, stuck to bottom Effervescence: slow, low intensity 30 sec, clear: 1 min 10 sec | | Big lumps, moist, coherent mass, stuck to bottom Effervescence: slow, low intensity 25 sec, clear: 1 min 15 sec |
| Day 2 | | hard cake, stuck to bottom Effervescence: Slow 22 sec, clear: 57 sec | | Hard, moist cake, stuck to bottom Effervescence: Slow, low intensity 15, clear: 1 min 20 sec |
| Day 3 | | Hard cake, stuck to bottom Effervescence: Slow, low intensity, 49 sec, clear: 1 min 47 sec. | | Hard, fused, moist mass, stuck to bottom Effervescence: Slow, low intensity, starts after 11 sec for 58 sec, clear: 1 min 20 sec |

EXAMPLE 20. EFFERVESCENT COMPOSITION CONTAINING ACID CO-CRYSTAL FOR ORALLY DISINTEGRATING TABLET

Objective

To explore the application of effervescent composition, where acid is present in co-crystal form, for Orally Disintegrating Tablet (ODT) formulation.

Introduction

Orally disintegrating tablets are the formulations which are supposed to disintegrate in the oral cavity within 60 seconds. Different super-disintegrants and their combinations have been used to ensure the disintegration of a tablet within 60 seconds.

We investigated the application of the novel effervescent compositions of the present invention in the ODT formulation and selected piroxicam as a model drug compound. We also used piroxicam in the form of piroxicam/glutaric acid co-crystal so that glutaric acid could participate in the effervescent action and to evaluate whether this in turn leads to fast disintegration of the ODT formulation.

The preparation of piroxicam-glutaric acid, 1:1 co-crystal was achieved as follows. Piroxicam (0.828 g) and glutaric acid (0.330 g) were taken in a mortar and subjected to liquid assisted grinding with ethanol for 5 min. The resultant product was characterised by X-ray diffractometry (XRD) to confirm the co-crystal formation. The composition is shown below for the piroxicam and piroxicam-glutaric acid co-crystal.

TABLE 39

| Name of ingredients | Piroxicam ODT | Piroxicam-glutaric acid co-crystal ODT |
| --- | --- | --- |
| Piroxicam | 20 mg | — |
| Piroxicam-glutaric acid co-crystal | | 28 mg |
| Citric acid-nicotinamide co-crystal | 82 mg | 82 mg |
| Sodium bicarbonate | 50 mg | 60 mg |
| Mannitol | 200 mg | 200 mg |
| Microcrystalline cellulose | 40 mg | 22 mg |
| Talc | 8 mg | 8 mg |

All ingredients listed in above table were sieved through #355μ. The amount of each ingredient required for one tablet was weighed accurately and mixed for 2 minutes to get the homogenous mixture. This mixture was then compressed under 0.5 Ton pressure with Dwell time of 10 sec. The tablets were stored at 75% and 98% relative humidity and tested for their physical appearance and disintegration performance. The disintegration test was performed using USP disintegration test apparatus with 900 ml distilled water as medium. Disintegration test was stopped when there is no particle on the mesh and the same was noted as a disintegration time.

TABLE 40

| | Piroxicam ODT | | | |
| --- | --- | --- | --- | --- |
| | 75% RH | | 98% RH | |
| Day | Physical appearance | Disintegration time | Physical appearance | Disintegration time |
| Day 0 | Smooth surface. White coloured tablet | 20-22 sec | | |
| Day 1 | Data not available | Data not available | Moist surface, slightly yellow tablet (this might be due to presence of other tablet ingredients like mannitol and MCC which absorbs moisture) | 50-55 sec |

TABLE 41

| | Piroxicam-glutaric acid co-crystal ODT | | | |
| --- | --- | --- | --- | --- |
| | 75% RH | | 98% RH | |
| Day | Physical appearance | Disintegration time | Physical appearance | Disintegration time |
| Day 0 | Smooth surface, white coloured tablet | 10-15 sec | | |
| Day 1 | Smooth surface, white coloured tablet | 10-15 sec | Moist surface, yellow tablet (this might be due to presence of other tablet ingredients like mannitol and MCC which absorbs moisture) | 50-55 sec |

EXAMPLE 21. EFFERVESCENT COMPOSITION CONTAINING ACID CO-CRYSTAL FOR DELAYED/PROLONGED ACTION

An effervescent composition with delayed/prolonged effervescence action was prepared. For certain effervescent formulations like bath salts, detergents, prolonged effervescent action will be beneficial and thus we aimed to prolong the effervescence action of our novel effervescent composition. This was achieved by adding a lipidic component like Gelucire® 39/01 during the co-crystal preparation.

The preparation of a citric acid-nicotinamide co-crystal was conducted as follows. Citric acid (1.92 g) and nicotinamide (2.442 g) were taken in a mortar and subjected to liquid assisted grinding with ethanol which contains 2% of Gelucire® 39/01 for 5 min. The resultant product was characterised by X-ray diffractometry (XRD) to confirm the co-crystal formation. The effervescent performance was then evaluated. The effervescent composition (2 g) was added rapidly in one portion to 1 L water under stirring at 100 rpm. The time of cessation of effervescence and the time to obtain a clear solution was noted. It was observed that the effervescent action was delayed by 20 to 25 seconds and was retained for prolonged time (~2 min.) as compared to effervescent composition with no addition of Gelucire® 39/01 during acid co-crystal formation.

EXAMPLE 22. DYNAMIC VAPOUR SORPTION (DVS) DATA FOR EFFERVESCENT COMPONENTS AND MIXTURES

The dynamic vapour sorption/desorption study was performed using DVS Intrinsic system with DVS-Intrinsic control software version 1.06.3 from Surface Measurement System Ltd. UK. The sample weights were taken in the range of 30-50 mg and below experimental parameters were kept constant for all samples.

TABLE 42

| Start Relative Humidity (RH) | 0% |
| --- | --- |
| End Relative Humidity (RH) | 90% |
| Step change | 10% |
| Time at each stage | dm/dt |
| Temperature | 25° C. |
| Full cycle with the above parameters. | |

Results of the dynamic vapour sorption study are shown in Table 43 below and in FIGS. 1 to 5.

This study shows deliquescent nature of the citric acid where citric acid undergoes liquefaction and shows total weight gain due to moisture sorption of 31%. FIG. 1 provides a graphical plot of the change in mass of the citric acid as the relative humidity increases.

Figure 2:
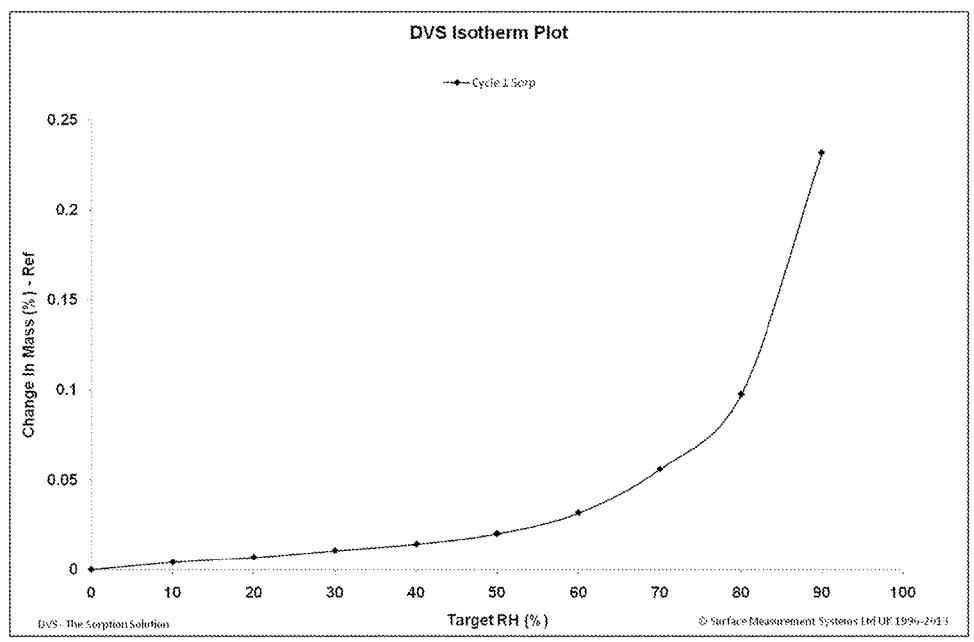
FIG. 2 shows the DVS study plot of the change in mass of citric acid:nicotinamide co-crystal against the relative humidity.
Figure 3:
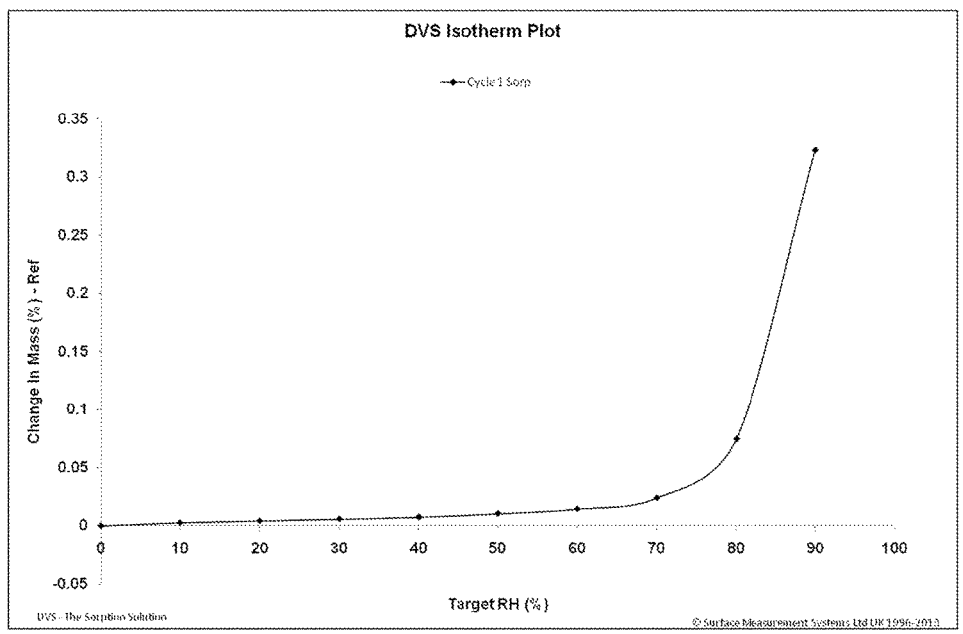
FIG. 3 shows the DVS study plot of the change in mass of sodium bicarbonate against the relative humidity.
Figure 4:
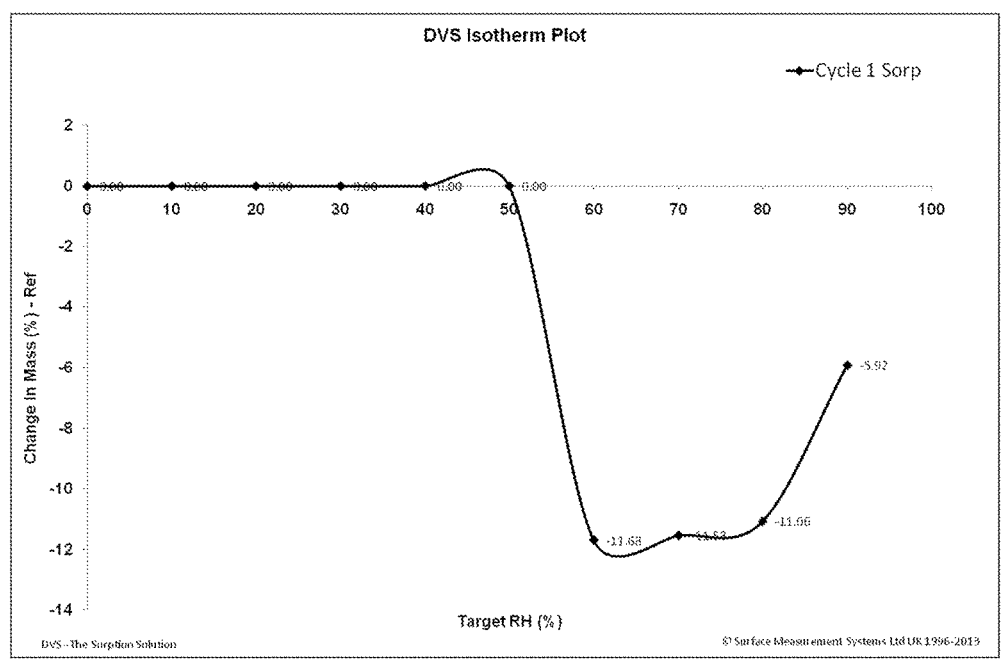
FIG. 4 shows the DVS study plot of the change in mass of a standard effervescent composition against the relative humidity. The standard effervescent composition contains the acid component in the free form.

On the other hand co-crystal of citric acid with nicotinamide is non-hygroscopic and absorbs only 0.23% moisture even at 90% relative humidity (RH). FIG. 2 shows the change in mass of the co-crystal as the relative humidity increases.

Alkali agent, sodium bicarbonate shows less moisture sorption tendency and shows weighed gain of 0.32% even at 90% relative humidity. The change in mass of the sodium bicarbonate as the humidity increases is outlined in FIG. 3.

A standard effervescent composition (where the acidic component i.e. citric acid is its free form) undergoes destabilisation during dynamic vapour sorption experiments. This is displayed in FIG. 4. The DVS isotherm shows that between 40% and 50% RH, the standard effervescent composition absorbs some moisture (less than 1%). This small amount of moisture is enough to initiate the effervescence reaction as reflected by the sample weight loss which is due to the loss of carbon dioxide in the effervescence reaction.

Figure 5:
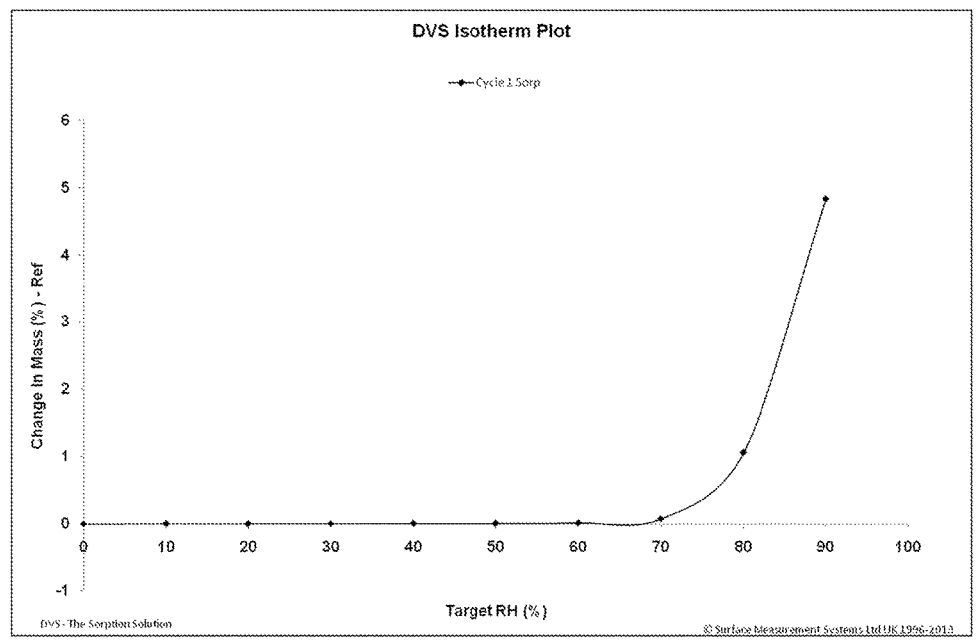
FIG. 5 shows the DVS study plot change in mass of an effervescent composition stabilised by having the acid component present in the form of a co-crystal.

The novel effervescent composition (where the acidic component i.e. citric acid is in the form of a co-crystal with nicotinamide) shows stability at all relative humidities despite a 4.8% weigh gain due to moisture absorption. FIG. 5 shows this. The results also indicate that the 4.8% of moisture is not enough to break the citric acid co-crystal; hence there is no free citric acid to take part in the effervescence reaction.

TABLE 43

| | Change In Mass (%) | | | | |
| --- | --- | --- | --- | --- | --- |
| Target Relative Humidity (%) | 1. Citric Acid | 2. Citric acid:nicotinamide, 1:2 co-crystal | 3. Sodium Bicarbonate | 4. Standard effervescent composition (where acid is in its free form) | 5. Stabilised effervescent composition (acid is in the form of co-crystal) |
| 0.0 | 0.00 | 0.0002 | −0.0001 | 0.00 | 0.000 |
| 10.0 | 0.00 | 0.0044 | 0.0027 | 0.00 | 0.003 |
| 20.0 | 0.00 | 0.0070 | 0.0042 | 0.00 | 0.004 |
| 30.0 | 0.00 | 0.0108 | 0.0056 | 0.00 | 0.006 |
| 40.0 | 0.00 | 0.0145 | 0.0074 | 0.00 | 0.007 |
| 50.0 | 0.00 | 0.0203 | 0.0103 | 0.00 | 0.008 |
| 60.0 | 0.01 | 0.0318 | 0.0143 | −11.68 | 0.017 |
| 70.0 | 0.02 | 0.0561 | 0.0240 | −11.53 | 0.077 |
| 80.0 | 4.65 | 0.0976 | 0.0746 | −11.06 | 1.063 |
| 90.0 | 31.21 | 0.2319 | 0.3236 | −5.92 | 4.829 |

The invention claimed is:

1. An effervescent composition comprising an acidic component and a basic component, wherein the acidic component is in the form of a co-crystal, wherein the co-crystal is not a hydrate or a co-crystal of VX-950:4-hydroxybenzoic acid, pterostilbene:glutaric acid, pterostilbene:caffeine, pterostilbene:carbamazepine or pterostilbene:piperazine.

2. An effervescent composition comprising an acidic component and a basic component, wherein the acidic component is in the form of a co-crystal, and wherein the composition includes one or more agents selected from the group consisting of an active pharmaceutical ingredient, a sterilising agent, a cleaning agent, a nutritional component, an agrochemical component and an animal health medicament, and optionally one or more excipients.

3. The composition of claim 1, wherein the acidic component which is formed into the co-crystal is selected from the group consisting of an organic acid, an organic acid salt, an organic acid anhydride, an inorganic acid, an inorganic acid salt, and mixtures of one or more of the above.

4. The composition of claim 1, wherein the acidic component is a carboxylic acid.

5. The composition of claim 4, wherein the carboxylic acid is selected from the group consisting of formic acid, propionic acid, malic acid, tartaric acid, citric acid, glycolic acid, maleic acid, fumaric acid, adipic acid, succinic acid, lactic acid, gluconic acid, fumaric acid, oxalic acid, glutaric acid, boric acid, sulphamic acid and similar sulphonic acids.

6. The composition of claim 1, wherein the basic component is selected from the group consisting of carbonates, bicarbonates and sesquicarbonates.

7. The composition of claim 6, wherein the basic component is one or more of carbonates, bicarbonates and sesquicarbonates in the form of their ammonium, alkali metal or alkaline earth salts.

8. The composition of claim 1, wherein the co-former component is selected from the group consisting of ascorbic acid, gallic acid, nicotinamide, isonicotinamide, citric acid, aglutamic acid, histidine, urea, saccharine, glycine, tyrosine, vanillin and valine.

9. The composition of claim 1, wherein the co-crystal and the basic component are present in a ratio of from 1:0.5 mole ratio of co-crystal (based on the acidic component) to 1:10 mole ratio.

10. The composition of claim 1, wherein the acidic component represents at least 30% by weight of the co-crystal.

11. The composition of claim 10, wherein the co-crystal comprises an acidic component and an acidic co-former, optionally the acidic component and acidic co-former making up about 100% by weight of the co-crystal.

* * * * *